US008356515B2

(12) United States Patent  
Druyts (10) Patent No.: US 8,356,515 B2  
(45) Date of Patent: Jan. 22, 2013

(54) METHOD AND SYSTEM FOR MEASURING A RHEOLOGICAL TRANSITION LEVEL

(75) Inventor: Marcus Philippus Maria Druyts, Bruges (BE)

(73) Assignee: M.D.C.E. BVBA and Demco NV (BE)

( * ) Notice: Subject to any disclaimer, the term of this patent is extended or adjusted under 35 U.S.C. 154(b) by 472 days.

(21) Appl. No.: 12/486,612

(22) Filed: Jun. 17, 2009

(65) Prior Publication Data

US 2010/0147055 A1  Jun. 17, 2010

(30) Foreign Application Priority Data

Jun. 20, 2008  (BE) .................................. 2008/0341

(51) Int. Cl.  
*G01B 21/18* (2006.01)

(52) U.S. Cl. .............. 73/291; 73/866.5; 33/755; 33/756

(58) Field of Classification Search ...... 73/12.04–12.13, 73/54.01, 54.23, 54.36, 81, 84, 85, 866.5, 73/290 R, 290 B, 290 V, 291–334, 170.32; 33/755, 756  
See application file for complete search history.

(56) References Cited

U.S. PATENT DOCUMENTS

| | | | | | |
|---|---|---|---|---|---|
| 2,464,834 | A | * | 3/1949 | Taylor | 73/291 |
| 3,139,147 | A | * | 6/1964 | Hays et al. | 175/233 |
| 3,206,979 | A | * | 9/1965 | Banks | 73/290 V |
| 3,298,222 | A | * | 1/1967 | Costello et al. | 73/84 |
| 3,455,151 | A | * | 7/1969 | Richard | 73/84 |
| 3,534,605 | A | * | 10/1970 | Koning et al. | 73/290 R |
| 3,721,124 | A | | 3/1973 | Franks | |
| 3,781,624 | A | * | 12/1973 | Tullis | 318/482 |
| 3,906,781 | A | * | 9/1975 | Vlasblom | 73/84 |
| 4,050,180 | A | * | 9/1977 | King | 43/27.4 |
| 4,056,887 | A | * | 11/1977 | Tucker et al. | 33/715 |
| 4,255,859 | A | * | 3/1981 | Klieman | 33/715 |
| 4,365,509 | A | * | 12/1982 | Cornelis | 73/290 V |
| 4,492,111 | A | * | 1/1985 | Kirkland | 73/84 |
| 4,786,846 | A | * | 11/1988 | Uchida | 318/482 |
| 4,875,295 | A | * | 10/1989 | Fleckenstein | 33/720 |
| 5,031,452 | A | * | 7/1991 | Dobson et al. | 73/304 R |
| 5,479,724 | A | * | 1/1996 | Nahajski et al. | 33/719 |
| 5,493,895 | A | * | 2/1996 | Cyr et al. | 73/12.13 |
| 5,533,392 | A | * | 7/1996 | Kira | 73/290 B |
| 5,681,982 | A | * | 10/1997 | Stoll et al. | 73/12.13 |
| 5,902,939 | A | * | 5/1999 | Ballard et al. | 73/863.12 |
| 5,921,328 | A | * | 7/1999 | Babineau et al. | 175/20 |
| 6,230,820 | B1 | * | 5/2001 | Cordry | 175/20 |

(Continued)

FOREIGN PATENT DOCUMENTS

BE  901687  5/1985

(Continued)

*Primary Examiner* — David Rogers  
(74) *Attorney, Agent, or Firm* — Bret E. Field; Benjamin C. Pelletier; Bozicevic, Field & Francis LLP (57) ABSTRACT

Method for measuring a rheological transition level between a first layer with first rheological properties, typically a fluid mud layer, and a second layer lying thereunder and having different, second rheological properties, typically a solid mud layer, wherein using a cable an object is lowered through the first layer into the second layer lying thereunder. A dynamic quantity of the moving cable with object, influenced by the rheological properties, or a change of this quantity, is measured. It is determined on the basis of this measurement when the object is located at the rheological transition level.

26 Claims, 7 Drawing Sheets

U.S. PATENT DOCUMENTS

| | | | |
|---|---|---|---|
| 6,427,529 B1 * | 8/2002 | Daly | 73/152.01 |
| 6,481,110 B1 * | 11/2002 | Butler | 33/393 |
| 6,575,114 B2 * | 6/2003 | Sandler et al. | 114/315 |
| 6,732,580 B2 * | 5/2004 | Dirksen | 73/149 |
| 6,820,701 B1 * | 11/2004 | Clark et al. | 175/49 |
| 7,040,146 B2 * | 5/2006 | Mackenzie et al. | 73/81 |
| 7,047,653 B2 * | 5/2006 | Fitzgerald | 33/304 |
| 7,464,589 B2 * | 12/2008 | Reeves | 73/299 |
| 7,938,002 B1 * | 5/2011 | Lazos | 73/290 B |
| 2006/0170543 A1 * | 8/2006 | Schaffer et al. | 340/521 |
| 2009/0308143 A1 * | 12/2009 | Boggess | 73/84 |

FOREIGN PATENT DOCUMENTS

| | | | |
|---|---|---|---|
| BE | 1015773 | | 8/2005 |
| EP | 138256 A2 | * | 4/1985 |
| EP | 0207038 | | 12/1986 |
| EP | 473366 A1 | * | 3/1992 |
| GB | 2070773 A | * | 9/1981 |
| GB | 2150694 A | * | 7/1985 |
| SU | 645053 A | * | 1/1979 |

* cited by examiner

METHOD AND SYSTEM FOR MEASURING A RHEOLOGICAL TRANSITION LEVEL

This application claims priority of Belgian patent application with application number BE 2008/0341 filed on Jun. 20, 2008.

FIELD OF THE INVENTION

The present invention relates to a method, a system and a sounding probe for measuring a rheological transition level between a first layer with first rheological properties, typically a fluid mud layer, and a second layer lying thereunder and having different, second rheological properties, typically a solid mud layer. The present invention relates particularly to such a method, system, and sounding probe for measuring the nautical bottom on the basis of a sounding/penetration measurement.

BACKGROUND

In a harbour or navigable channel the mud layer generally consists of a fluid mud layer and a consolidated (solid) mud layer. The transition between these layers is a rheological transition level which can be deemed as the real nautical bottom. It is particularly important for shipping traffic to know the exact depth at which this transition is located.

The prior art already comprises a number of techniques for measuring the nautical bottom, wherein a distinction is made between a measurement in which an object is towed, and a sounding/penetration measurement at a determined location.

The Belgian patent with publication number 1015773 in the name of applicant thus describes a solution in which the nautical bottom is measured using a continuously towed random body.

Figure 1A:
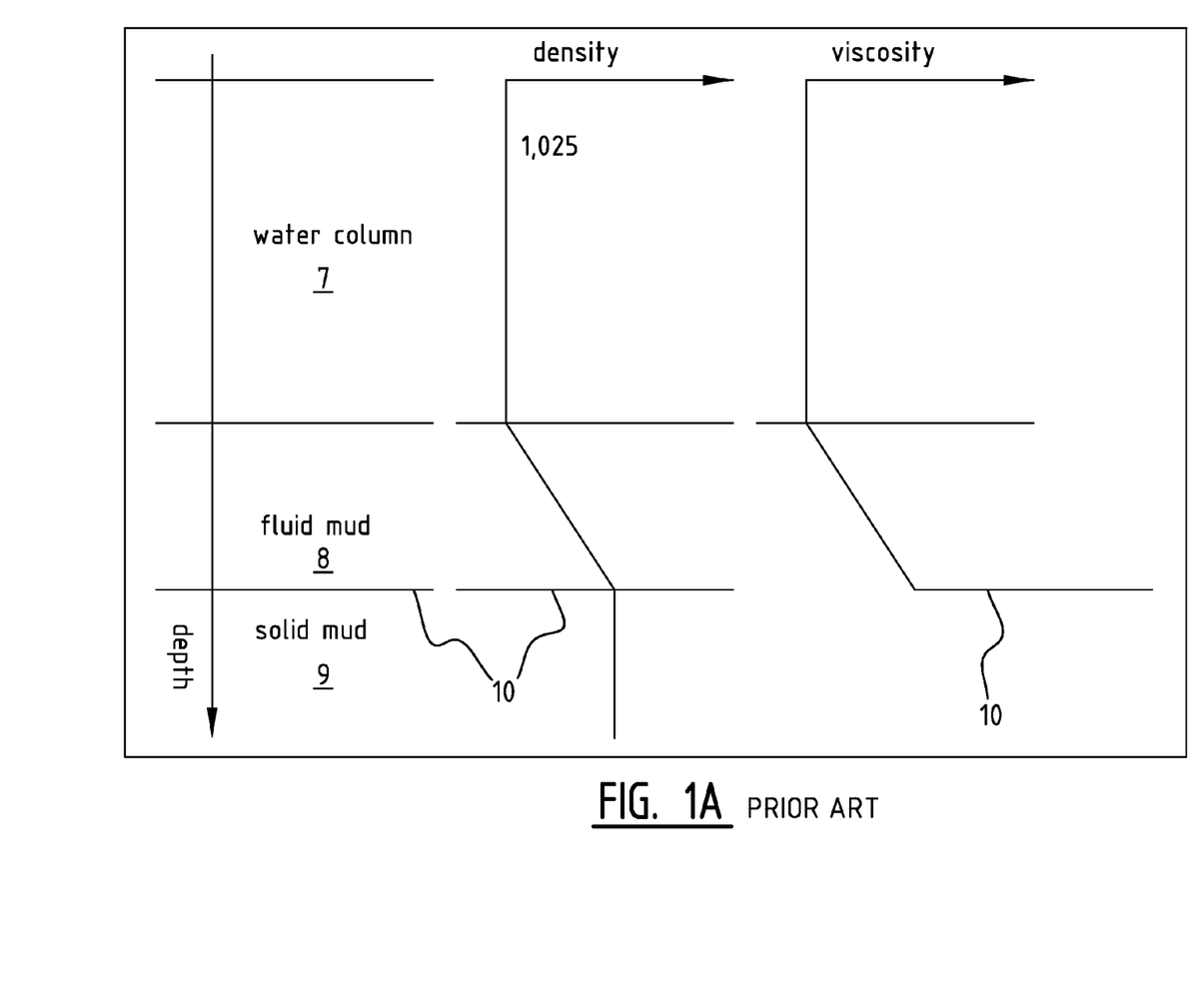
FIG. 1A shows diagrams of the density and the viscosity in a typical navigable channel or harbour.
Figure 1B:
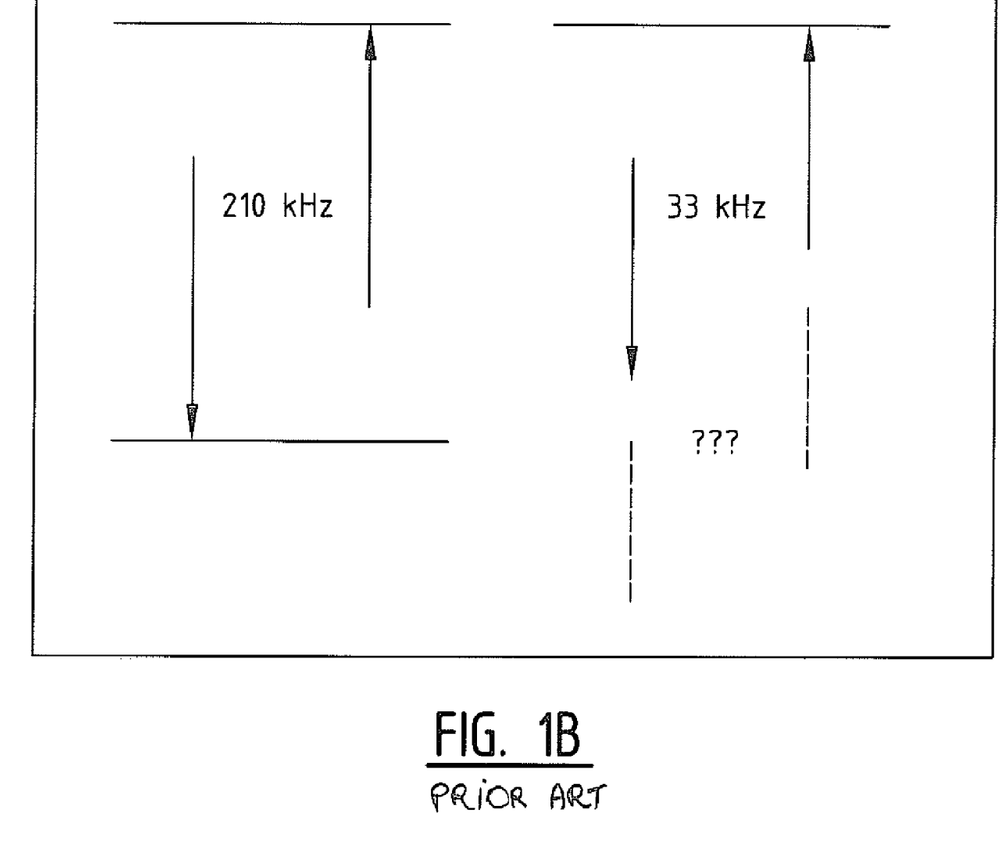
FIG. 1B illustrates a prior art method which makes use of acoustic signals.

It is also known to use acoustic signals to determine the depth of the rheological transition level. As illustrated in FIGS. 1A and 1B, this leads to inaccurate results. At a relatively high frequency of 210 kHz the acoustic signal is reflected at the top of the fluid mud layer 8 and not at the rheological transition level 10. At lower frequencies the level at which reflection takes place is uncertain. Such a measurement does not therefore allow of accurate determination of the location of the transition.

Further known is a so-called Navitracker which performs an up and downward movement in the mud. The density of the mud layer is measured in the Navitracker using a radioactive source. The Navitracker cannot however be introduced into the solid mud layer and cannot therefore determine the rheological transition level. An analogous technique is used in the so-called sounding/penetration probes, where the probe is carried through the fluid mud layer to a position in the vicinity of the solid mud layer while the density is measured. The density at the end of the fluid mud layer 8 is however substantially the same as the density in the solid mud layer 9 (see FIG. 1A), so that the rheological transition cannot be accurately determined.

SUMMARY

The present invention has for its object to provide a method and system of the type stated in the preamble for determining the location of the rheological transition level in accurate manner.

Provided for this purpose is a method which is distinguished in that using a cable an object is lowered through the first layer into the second layer lying thereunder, wherein a dynamic quantity of the moving cable with object, influenced by the rheological properties, or a change in this quantity, is measured, and wherein it is determined on the basis of this measurement when the object is located at the rheological transition level.

When an object is lowered via a cable, a number of dynamic quantities are then involved, such as the force in the cable and the velocity at which the cable is lowered. These dynamic quantities are partly determined by the rheological properties of the layers. The location of the rheological transition level can thus be determined with high precision by detecting a change in such a quantity; this is because the length along which the cable has been lowered determines the depth of the rheological transition level.

According to a first possible embodiment, the force or change in force in the cable (or a variable representative thereof) is the dynamic quantity which is measured, and the velocity at which the cable is lowered is controlled. The velocity is then preferably held within a determined range, this range being such that the force in the cable displays a clear jump at the transition from the first layer to the second. Still more preferably the velocity is held substantially constant at a velocity considerably lower than the equilibrium velocity for the first layer, for which the gravitational force of the object is equal to the upward force encountered by the object during lowering.

According to a particularly advantageous embodiment, the velocity at which the object is lowered is adjusted such that the cable becomes slack (limp) in the second layer, wherein the slackness of the cable is measured, for instance by a slack cable switch.

According to a second embodiment, the velocity at which the cable descends is measured, while the force in the cable is controlled. The force in the cable is preferably held here within a determined range, this range preferably being chosen such that the change in velocity at the transition from the first layer to the second can be readily measured. The force is still more preferably held substantially constant at a value for which the velocity in the second layer is greater than a determined critical value, and is for instance greater than 0.25 m/s.

According to the preferred embodiment of the invention, the object has an average density greater than the density of the first layer and also greater than the density of the second layer. The object is preferably manufactured from a rather heavy material such as steel, and preferably has a shape which impedes the flow around the object little, such as a spherical shape.

The present invention further relates to a system which is distinguished in that the system comprises:
- a lowering/hoisting device with a cable and with control means for controlling the lowering;
- an object connected to this cable and having an average density greater than that of the first and second layer;
- measuring means for measuring a dynamic variable of the lowering/hoisting device influenced by the rheological properties, this such that it is possible to determine from the dynamic variable measured by the measuring means that the object is situated at the rheological transition level.

According to a first embodiment, the control means are adapted to control the lowering velocity, and the measuring means are adapted to measure the force or a change in force in the cable (or a variable representative thereof). This preferably takes place in accordance with the first embodiment of the above described method.

In the case of a change in force a slack cable switch can for instance be used. Another option consists of measuring a parameter of the motor of the lowering/hoisting device representative of the force (voltage/current in the case of a linear motor; pressure/flow rate in the case of a hydraulic motor).

According to a second embodiment, the control means are adapted to control the force in the cable during lowering, and the measuring means are adapted to measure the lowering velocity. This preferable takes place in accordance with the second embodiment of the above described method.

According to a possible embodiment, the lowering/hoisting device is provided with measuring means for measuring the length of the lowered cable.

According to another option, wherein water is situated above the first layer, the object is provided with pressure measuring means for measuring the pressure exerted by the water column at the rheological transition level, in order to derive herefrom the depth of the rheological transition level. The water pressure can for instance then be carried to the position of the object through a tube, the outer end of which is situated in the water above the first layer.

The invention further relates to a sounding probe for measuring a rheological transition level between a first layer with first rheological properties, typically a fluid mud layer, and a second layer lying thereunder and having different, second rheological properties, typically a solid mud layer.

An embodiment of the sounding probe comprises:
a substantially probe shaped body;
measuring means for measuring a dynamic variable of said body when moving, typically descending, through the first and second layer, or a change of said variable, said dynamic variable being influenced by the rheological properties, such that it is possible to determine from the dynamic variable measured by the measuring means that the object is situated at the rheological transition level.

According to a preferred embodiment of the system or sounding probe the measuring means consist of an accelerometer for measuring the acceleration of the body moving through the first and second layer, or a means for measuring the velocity of the moving body. Such an accelerometer can easily be included in the body of the probe.

According to a preferred embodiment the body is provided with weight sufficient to allow the probe to descend at an acceptable speed through the first and second layer.

According to a further developed embodiment of the sounding probe, the probe further comprises a pressure sensor for measuring the hydrostatic water pressure at the location of the probe. In that way, the depth position of the probe can be determined. The sensor is preferably taken up in an isolated housing with pressure tubes extending upwards along the cable. The length of the pressure tube is preferably such that in use the housing communicates with a water layer above the first layer.

The invention will be further elucidated on the basis of a number of non-limitative exemplary embodiments with reference to the accompanying drawing.

DETAILED DESCRIPTION OF THE PREFERRED EMBODIMENTS

A body which is immersed in a fluid and is free-floating is subjected to two forces:
a downward directed gravitational force acting on the apparent weight of the body, this being its own weight minus the weight of the displaced fluid;
an upward directed force caused by the flow of the fluid around the body.

Figure 4:
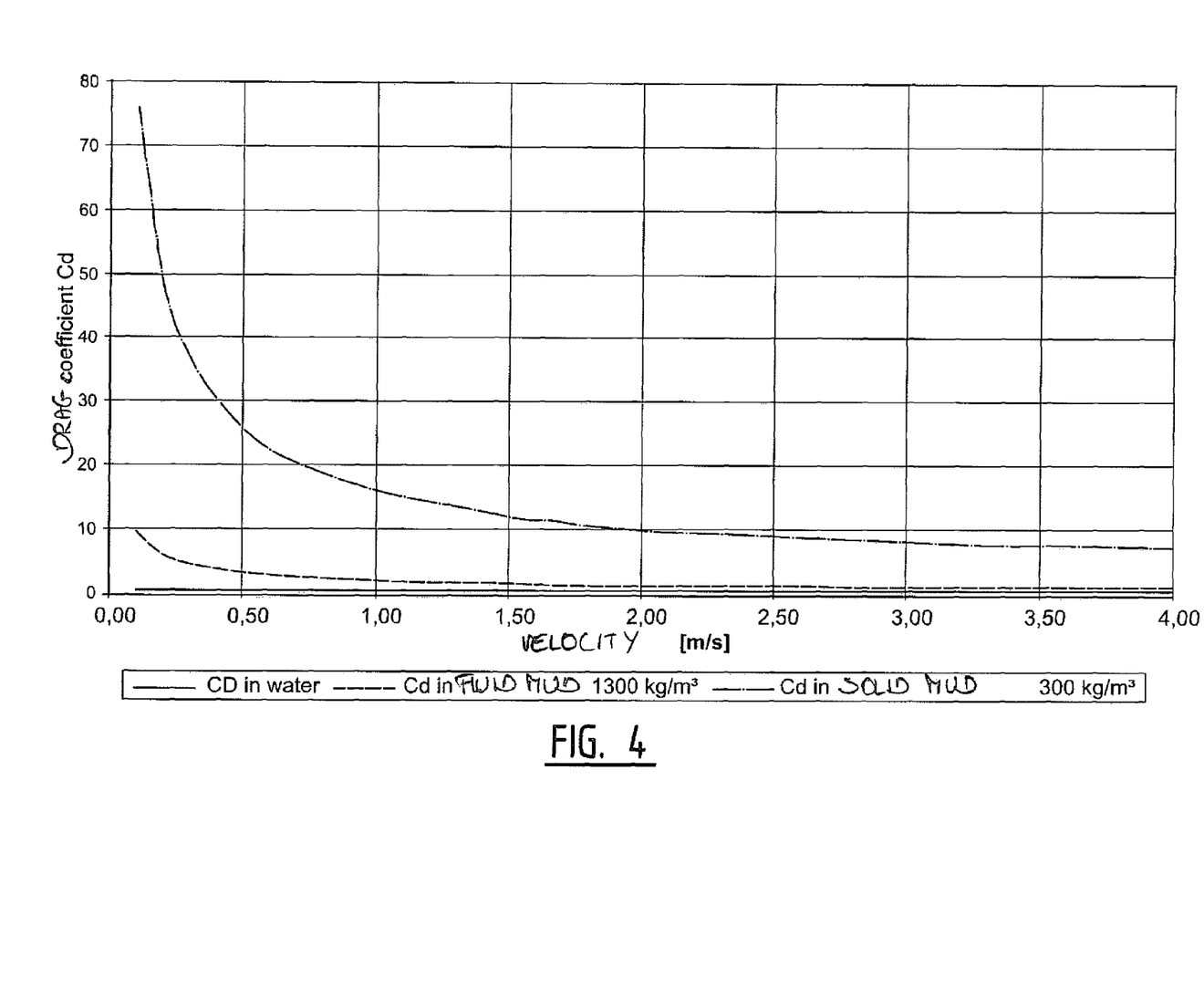
FIG. 4 shows a graph of the drag coefficient as a function of the velocity for water, fluid mud and solid mud.

The upward directed force generated by the rheological properties, and in particular by the viscosity of the material through which the body is moving, is calculated with the following formula:

$$F_v = C_d \cdot 1/2 \cdot \rho \cdot v^2 \cdot A$$

wherein $F_v$ is the force in Newton, $C_d$ is the drag coefficient, $\rho$ the density in kg/m$^3$, v the lowering velocity in m/s and A the surface area of the cross-section perpendicularly of the lowering velocity. The drag coefficient of the body is in turn determined by the shape of the body, the roughness of the body and the Reynolds number (the viscosity). FIG. 4 illustrates the drag coefficient as a function of the velocity for respectively water, fluid mud and solid mud.

When the upward force is equal to the downward force, the body will descend at constant velocity; this velocity is referred to as the equilibrium velocity.

Figure 5A:
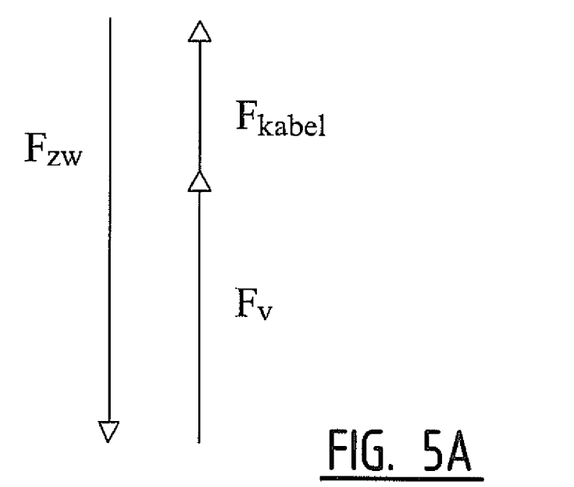
FIGS. 5(A) and (B) show a diagram of the forces acting on the object during lowering.
Figure 5B:
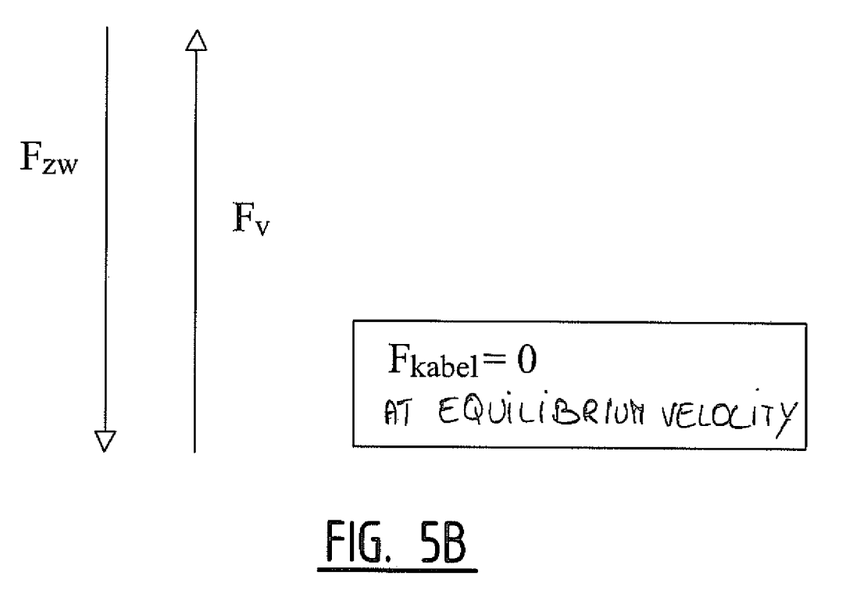

A body which is attached by means of the cable to a lowering/hoisting device will also be subjected in determined cases to a third force, i.e. the force exerted by the cable on the body. This cable force will depend on the velocity at which the cable is lowered:
when the lowering velocity is less than the equilibrium velocity (see FIG. 5A), a force $F_{kabel}$ will then occur in the cable which compensates the difference between the gravitational force $F_{zw}$ and the upward force $F_v$, and the cable remains tensioned.
when the lowering velocity is greater than or equal to the equilibrium velocity (see FIG. 5B), the force in the cable $F_{kabel}$ will disappear and, at a higher lowering velocity, the cable will gain on the body, i.e. the cable becomes slack.

The above formula shows that, at the same lowering velocity, the body in a fluid of high viscosity will be subject to a low suspension force (cable force), while in a fluid of low viscosity the body is subject to a high suspension force. Inversely, at the same cable force the body will displace more slowly in the fluid of high viscosity than in the fluid of low viscosity.

In the case of a navigable channel or harbour there are typically two phases present in the mud layer located under water column 7 (see FIG. 1A):
the fluid mud phase 8 with a low viscosity;
the solid mud phase 9 with a very high viscosity.

Figure 3:
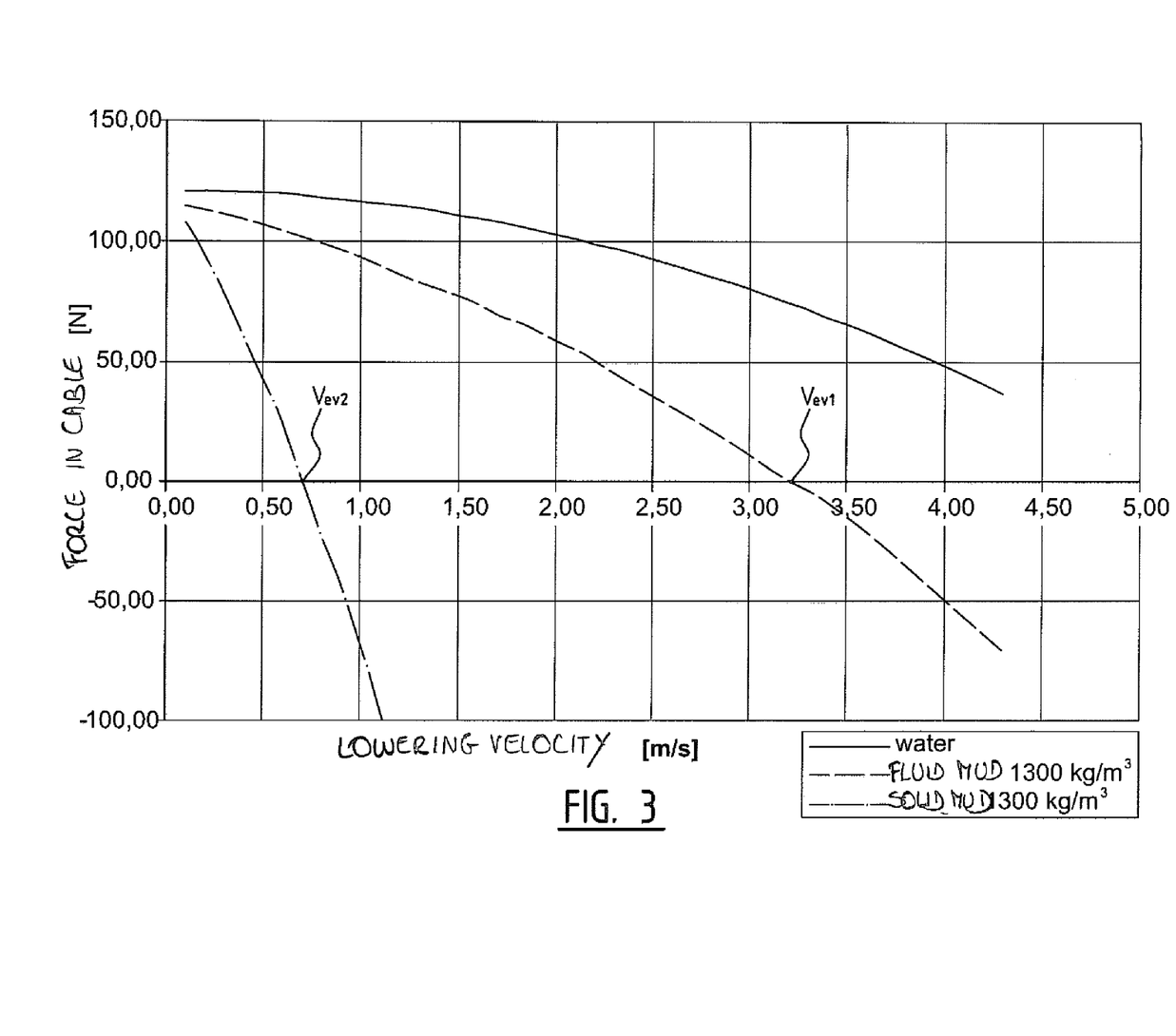
FIG. 3 shows a graph of the force in the cable as a function of the lowering velocity for a sphere lowered respectively into water, fluid mud and solid mud.

FIG. 3 illustrates the cable force as a function of the velocity for an object moving respectively through water column 7, through fluid mud layer 8 and through the solid mud layer 9. At a constant velocity the force in the cable is considerably lower for solid mud when compared to water or fluid mud.

The above described physical principles are employed in the method and the system according to the invention described hereinbelow with reference to FIG. 2.

Figure 2:
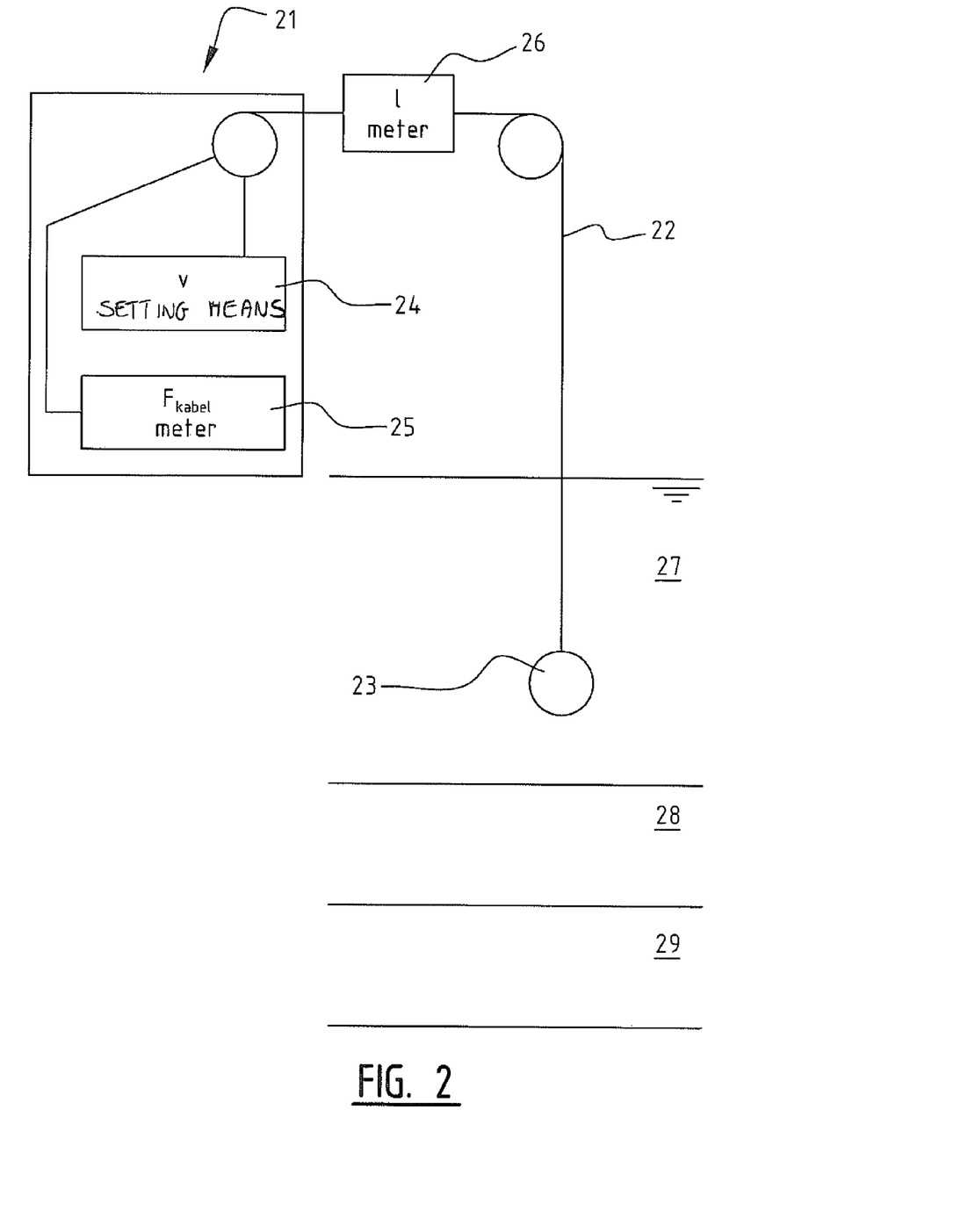
FIG. 2 shows a schematic representation of an embodiment of a system according to the invention.

According to the exemplary embodiment of FIG. 2, the system comprises a lowering/hoisting device 21 with a cable 22, to the outer end of which a steel sphere 23 is attached. The lowering/hoisting device is provided with means 24 for setting the lowering velocity v. Means 25 are further provided for measuring the force in the cable $F_{kabel}$. Finally, measuring means 26 are provided for measuring the length of the lowered cable. When sphere 23 is lowered into a typical navigable channel, it will move first through water column 27, then through the first layer 28 of low viscosity and into the second layer 29 of high viscosity.

The lowering velocity is preferably lower than the equilibrium velocity in the fluid mud $v_{ev1}$ and greater than the equilibrium velocity in the solid mud $v_{ev2}$ (see FIG. 3). In this way cable 22 will be tensioned when the sphere passes through first layer 28, while the cable becomes slack when the sphere moves through second layer 29. Such a slackening of the cable can be measured easily and accurately such that the exact location of the transition between the first and the second layer can be precisely determined, for instance on the basis of the measurements performed by measuring means 26.

Figure 6:
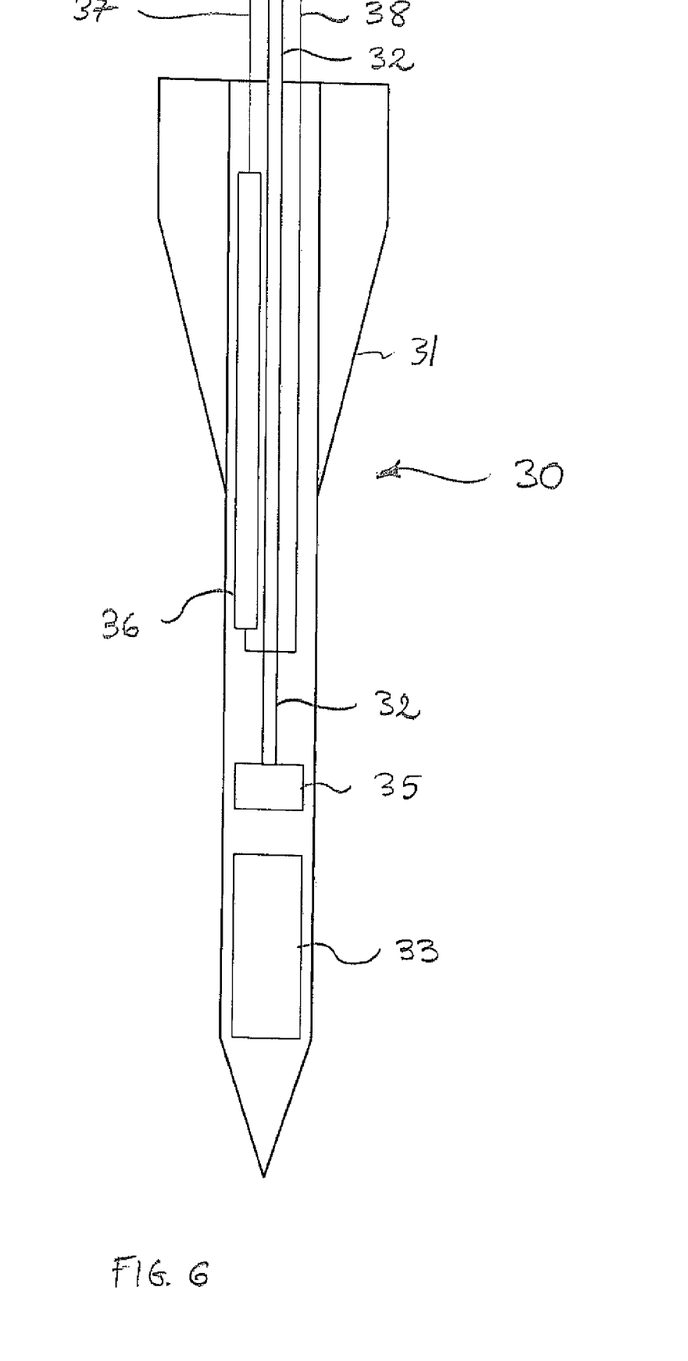
FIG. 6 is a schematic view of a sounding probe according to an embodiment of the invention.

FIG. 6 illustrates an embodiment of a sounding probe according to the invention. The probe 30 has a hollow probe shaped body 31. At the lower side of the probe 30 a weight 33 is included inside the body 31. Further, an accelerometer 35 is contained inside the body 31. Signals measured by the accelerometer 35 are transferred to processing means (not shown), e.g. through electric wiring passing through cable 32. It is also an option to provide a pressure sensor, e.g. a CTD (Conductivity Temperature Depth recorder) device 36 at the probe 30. This device is preferably taken up in an isolated space communicating via tubes 37, 38 with a higher layer, preferably a water layer, so that the pressure sensor 36 can measure the hydrostatic water pressure, undisturbed by the density of the first layer. The measurement signals from the CTD device can also be transmitted via electric wiring through cable 32.

The skilled person will appreciate that the invention is not limited to the above described exemplary embodiment and that many variants can be envisaged, wherein for instance the force in the cable is held constant and the change in the lowering velocity is measured. The skilled person will further appreciate that the invention is not limited to measuring the nautical bottom, but that the method and the system can likewise be applied for the purpose of determining a random rheological transition between a first layer of a first viscosity and a second layer of a second, different viscosity. The scope of protection is therefore defined solely by the following claims.

The invention claimed is:

1. A method for measuring a rheological transition level between a first fluid mud layer with first rheological properties, and a second consolidated mud layer lying thereunder and having different, second rheological properties, said method comprising:
   lowering an object through the first fluid mud layer into the second consolidated mud layer lying thereunder, using a cable;
   measuring either a dynamic quantity or a change of the dynamic quantity of the moving cable as the object moves from the first fluid mud layer into the second consolidated mud layer, with the attached object being influenced by the rheological properties; and
   on the basis of this measurement determining when the object is located at the rheological transition level.

2. The method of claim 1, wherein the first fluid mud layer has a first density and the second consolidated mud layer has a second density, and wherein the object has an average density greater than the first density and greater than the second density.

3. The method of claim 1, wherein a length over which the cable has been lowered is measured for the position in which the determined rheological transition level has been established.

4. The method according to claim 1, wherein the method further comprises measuring either a dynamic quantity or a change of the dynamic quantity of the moving cable as it moves through the first fluid mud layer.

5. The method according to claim 1, wherein the method further comprises measuring either a dynamic quantity or a change of the dynamic quantity of the moving cable as it moves through the second consolidated mud layer.

6. The method of claim 1, wherein the velocity at which the cable descends, or a variable linked thereto, is measured, whilst controlling the force in the cable.

7. The method of claim 6, wherein the force in the cable is held substantially constant while the cable is lowered through the first fluid mud layer and into the second consolidated mud layer.

8. The method of claim 6, wherein the force in the cable is held within a determined range while the cable is lowered through the first fluid mud layer and into the second consolidated mud layer.

9. The method of claim 8, wherein the force in the cable is set to a value for which the velocity in the second consolidated mud layer is greater than a determined critical value, for instance greater than 0.25 m/s.

10. The method of claim 1, wherein the dynamic quantity influenced by the rheological properties of the first fluid mud layer and the second consolidated mud layer is the force in the cable itself or a variable linked thereto, wherein during the descent of the object this dynamic quantity is measured while the velocity at which the cable is lowered through the first fluid mud layer and into the second consolidated mud layer is controlled.

11. The method of claim 10, wherein the velocity at which the object is lowered is such that the cable becomes slack in the second consolidated mud layer, wherein the measurement of the change in force in the cable consists of detecting the slackness of the cable.

12. The method of claim 10, wherein the velocity at which the cable is lowered through the first fluid mud layer and into the second consolidated mud layer is held constant.

13. The method of claim 10, wherein the velocity at which the cable is lowered through the first fluid mud layer and into the second consolidated mud layer is held within a determined range.

14. The method of claim 13, wherein the cable is lowered at a velocity considerably lower than an equilibrium velocity for the first fluid mud layer, for which equilibrium velocity the gravitational force of the object is equal to the upward force exerted on the object during descent.

15. A system for measuring a rheological transition between a first fluid mud layer with first rheological properties, and a second consolidated mud layer lying thereunder and having second rheological properties, comprising:
   a lowering/hoisting device with a cable and with control means for controlling the lowering;

an object connected to the cable and having an average density greater than that of the first fluid mud layer and the second consolidated mud layer;

measuring means adapted to measure either a dynamic variable or a change in the dynamic variable related to the lowering/hoisting device; and determining means adapted to determine when the object is at the rheological transition level based on the result from the measuring means obtained when the object moves from the first fluid mud layer into the second consolidated mud layer.

16. The system of claim 15, wherein the control means are adapted to control the lowering velocity and the measuring means are adapted to measure a variable determining the force or a change in force in the cable.

17. The system of claim 15, wherein the measuring means are a slack cable switch.

18. The system of claim 15, wherein the lowering/hoisting device is provided with a motor, the measuring means being adapted to measure a parameter of the motor representative of the force in the cable.

19. The system of claim 15, wherein the control means are adapted to control the force in the cable during lowering, and the measuring means are adapted to measure the lowering velocity.

20. The system of claim 15, wherein the lowering/hoisting device is provided with cable length measuring means for measuring the length of the lowered cable.

21. The system of claim 15, wherein the object is a steel sphere or wherein the object has a probe shaped body.

22. A sounding probe for measuring a rheological transition between a first fluid mud layer with first rheological properties, and a second consolidated mud layer lying thereunder and having second rheological properties, comprising:

an elongate body with a probe tip;

measuring means adapted to measure either a dynamic variable or a change in the dynamic variable related to the sounding probe; and determining means adapted to determine when the sounding probe is at the rheological transition level based on the result from the measuring means obtained when the sounding probe moves from the first fluid mud layer into the second consolidated mud layer.

23. The sounding probe of claim 22, wherein said measuring means is a measuring means for measuring the velocity or the acceleration of the sounding probe.

24. The sounding probe of claim 22, further comprising pressure measuring means for measuring the pressure exerted by the water column at the rheological transition level, in order to derive therefrom the depth of the rheological transition level.

25. A method for measuring a rheological transition level between a first fluid mud layer with first rheological properties, and a second consolidated mud layer lying thereunder and having different, second rheological properties, said method comprising:

lowering an object through the first fluid mud layer into the second consolidated mud layer lying thereunder, using a cable;

measuring either the force in the cable itself or a variable linked thereto as the object moves from the first fluid mud layer into the second consolidated mud layer, wherein during the descent of the object said force or said variable linked thereto is measured while the velocity at which the cable is lowered through the first fluid mud layer and into the second consolidated mud layer is controlled; and on the basis of this measurement, determining when the object is located at the rheological transition level.

26. A method for measuring a rheological transition level between a first fluid mud layer with first rheological properties, and a second consolidated mud layer lying thereunder and having different, second rheological properties, said method comprising:

lowering an object through the first fluid mud layer into the second consolidated mud layer lying thereunder, using a cable;

measuring either the velocity at which the cable descends, or a variable linked thereto as the object moves from the first fluid mud layer into the second consolidated mud layer, whilst controlling the force in the cable; and on the basis of this measurement, determining when the object is located at the rheological transition level.

* * * * *